United States Patent
Bernard et al.

(10) Patent No.: US 12,280,191 B2
(45) Date of Patent: Apr. 22, 2025

(54) SOLUTION VERIFICATION PRIOR TO THERAPY IN RENAL INSUFFICIENCY TREATMENT

(71) Applicant: GAMBRO LUNDIA AB, Lund (SE)

(72) Inventors: Steve Bernard, Eden Prairie, MN (US); Timothy Nadolski, Maple Grove, MN (US); John J. O'Mahony, Plymouth, MN (US)

(73) Assignee: Gambro Lundia AB, Lund (SE)

( * ) Notice: Subject to any disclaimer, the term of this patent is extended or adjusted under 35 U.S.C. 154(b) by 349 days.

(21) Appl. No.: 17/798,365

(22) PCT Filed: Feb. 10, 2021

(86) PCT No.: PCT/EP2021/053165
§ 371 (c)(1),
(2) Date: Aug. 9, 2022

(87) PCT Pub. No.: WO2021/160652
PCT Pub. Date: Aug. 19, 2021

(65) Prior Publication Data
US 2023/0106252 A1 Apr. 6, 2023

Related U.S. Application Data

(60) Provisional application No. 62/972,176, filed on Feb. 10, 2020.

(30) Foreign Application Priority Data

Mar. 11, 2020 (SE) .................................. 2050270-4

(51) Int. Cl.
A61M 1/16 (2006.01)
A61M 1/36 (2006.01)
A61M 1/14 (2006.01)

(52) U.S. Cl.
CPC ...... *A61M 1/1668* (2014.02); *A61M 1/36225* (2022.05); *A61M 1/1566* (2022.05);
(Continued)

(58) Field of Classification Search
CPC .... A61M 1/14; A61M 1/1566; A61M 1/1668; A61M 1/36225; A61M 2205/14;
(Continued)

(56) References Cited

U.S. PATENT DOCUMENTS 5,658,456 A 8/1997 Kenley
6,468,424 B1 10/2002 Donig
(Continued)

FOREIGN PATENT DOCUMENTS

WO WO 2009/006491 1/2009
WO WO 2019/129719 7/2019

OTHER PUBLICATIONS

International Search Report for PCT/EP2021/053165 dated Apr. 19, 2021 (2 pages).

*Primary Examiner* — Dirk R Bass
(74) *Attorney, Agent, or Firm* — Mueting Raasch Group

(57) ABSTRACT

Systems and methods for renal insufficiency treatment that include identifying and associating a solution container with a container support in the systems and methods are described herein. The systems and methods may associate an identified solution with an identified container support and verify compatibility of that combination with a selected treatment to reduce the likelihood for errors during setup and use of the systems and methods.

23 Claims, 6 Drawing Sheets

(52) U.S. Cl.
 CPC . *A61M 2205/3393* (2013.01); *A61M 2205/50* (2013.01); *A61M 2205/6009* (2013.01); *A61M 2205/6063* (2013.01)

(58) Field of Classification Search
 CPC .......... A61M 2205/18; A61M 2205/27; A61M 2205/3393; A61M 2205/50; A61M 2205/6009; A61M 2205/6063
 See application file for complete search history.

(56) References Cited

U.S. PATENT DOCUMENTS

| | | |
|---|---|---|
| 2010/0282834 A1 | 11/2010 | Devergne |
| 2010/0315231 A1 | 12/2010 | Rada |
| 2012/0138533 A1 | 6/2012 | Curtis |
| 2013/0062404 A1 | 3/2013 | Devergne |

SOLUTION VERIFICATION PRIOR TO THERAPY IN RENAL INSUFFICIENCY TREATMENT

This application is a U.S. National Stage Application of International Application No. PCT/EP2021/053165 filed Feb. 10, 2021, which was published in English on Aug. 19, 2021 as International Publication No. WO 2021/160652 A1. International Application No. PCT/EP2021/053165 claims priority to U.S. Patent Application No. 62/972,176 filed Feb. 10, 2020 and Swedish Application No. 2050270-4 filed Mar. 11, 2020.

The disclosure herein relates to renal insufficiency treatment. More particularly, the disclosure relates to systems and methods for renal insufficiency treatment that include identifying and associating a solution container with a container support in the systems and methods.

Patients with renal insufficiency may need supporting treatment in the form of dialysis for the removal of waste substances and excess of fluid from the body. Dialysis is a process to remove fluid and waste products from the patient by the use of diffusional or convective transport. Various dialysis techniques with associated dialysis fluids may be differentiated. Which dialysis technique to use, depends on the patient needs, treatment demands and available resources.

In a variety of renal insufficiency treatments, one or more fluids, or liquids, may be supplied to the renal insufficiency treatment system for use during the treatments and one or more fluids may be collected as a part of the treatments. Both the supplied and collected fluids may be stored in one or more reservoirs or containers. These reservoirs/containers may, during the course of treatment of a single patient, need to be replaced as they are either emptied (in the case of fluids supplied as a part of the treatment) or are filled to capacity (in the case of fluids collected as a part of the treatment).

SUMMARY

Systems and methods for renal insufficiency treatment that include identifying and associating a solution container with a container support in the systems and methods are described herein.

In one or more embodiments, the systems and methods may associate an identified solution with an identified container support and verify compatibility of that combination with a selected treatment to reduce the likelihood for errors during setup and use of the systems and methods. This may be particularly true for systems/treatments that require an operator to provide and/or replace containers holding specific fluids prior to and during treatment. Each container may need to be positioned at a specific location in the system (e.g., on a scale or support) and/or connected in a specific manner for a specific treatment therapy and failure to ensure that containers provide the correct fluids, are properly located (e.g., on a scale or other support), and/or properly connected may result in insufficient treatment and/or injury to a patient. The systems and methods described herein may reduce the likelihood for such errors in container selection/loading and/or placement on the system by providing for verification that containers holding the correct fluids are provided in the correct locations on a treatment system during setup and/or container replacement.

A first aspect of a renal insufficiency treatment system includes, in one or more embodiments, a renal insufficiency treatment apparatus comprising a plurality of container supports; a plurality of solution containers configured to be supported by the plurality of container supports, wherein each solution container comprises a machine readable solution indicator configured to identify solution in the solution container; a sensor configured to read the machine readable solution indicators on solution containers; computing apparatus comprising one or more processors, the computing apparatus operably coupled to the renal insufficiency treatment apparatus and the sensor. The computing apparatus is configured to: receive one or more signals from the sensor; identify a container support of the plurality of container supports based on a support signal received by the computing apparatus; identify solution in a solution container of the plurality of solution containers based on a solution signal received from the sensor in response to reading the machine readable solution indicator associated with the solution container, the solution signal being received by the computing apparatus; associate the identified solution with the identified container support; verify, based at least in part on the association between the identified solution and the identified container support, that the identified solution in the solution container associated with the identified container support is compatible with a selected treatment to be performed by the renal insufficiency treatment system; and activate an alert apparatus if the identified solution in the solution container associated with the identified container support is not compatible with the selected treatment.

As described herein, a renal insufficiency treatment system may include one of a blood pump configured to move blood through an extracorporeal circuit during extracorporeal renal insufficiency treatment and a peritoneal dialysis fluid pump configured to deliver dialysis fluid to a patient during a peritoneal renal insufficiency treatment depending on the type of renal insufficiency treatment system (i.e., an extracorporeal blood treatment system would include a blood pump and a peritoneal dialysis system would include a peritoneal dialysis fluid pump).

In a $2^{nd}$ aspect according to aspect 1, the system includes a plurality of machine readable support indicators, wherein each machine readable support indicator of the plurality of machine readable support indicators is associated with and configured to identify one container support of the plurality of container supports, wherein the container support is identified based on the support signal received from the sensor in response to reading the machine readable support indicator associated with the container support.

In a $3^{rd}$ aspect according to aspect 1, the container support is operably coupled to the computing apparatus and configured to provide the support signal to the computing apparatus, wherein the support signals for each container support of the plurality of container supports are generated by moving each container support between an open configuration and a closed configuration, wherein each container support is configured to receive a solution container when in the open configuration.

In a $4^{th}$ aspect of any one of aspects 1 to 3, the computing apparatus is configured to associate an identified solution with an identified container support for the first support signal received after the solution signal is received for the identified solution.

In a $5^{th}$ aspect of any one of aspects 1 to 3, receiving one or more signals from the sensor comprises receiving a first pair of consecutive support and solution signals from the sensor, wherein identifying a container support and identifying solution comprise identifying a first pair of container support and solution, and wherein associating the identified solution with the identified container support comprises associating the first identified solution with the first identified container support.

In a 6th aspect according to aspect 5, receiving one or more signals from the sensor further comprises receiving a second pair of consecutive support and solution signals from the sensor, wherein identifying a container support and identifying solution comprise identifying a second pair of container support and solution, and wherein associating the identified solution with the identified container support comprises associating the second identified solution with the second identified container support.

In a 7th aspect according to aspect 6, the computing apparatus is further configured to identify the selected treatment based on the first and second pairs of associated identified solutions and identified container supports.

In an 8th aspect according to any one of aspects 1 to 7, each container support of the plurality of container supports comprises a scale configured to weigh a solution container supported on the container support, wherein each container support is operably coupled to the computing apparatus, and wherein the computing apparatus is configured to receive a weight signal from each container support that is indicative of a weight of a solution container on the container support.

In a 9th aspect according to aspect 8, the computing apparatus is configured to associate an identified solution with an identified container support only if, after identifying a solution and identifying a container support, a weight signal is received from the identified container support before a subsequent solution signal or a subsequent support signal is received by the computing apparatus.

In a 10th aspect according to any one of aspects 1 to 9, wherein one container support of the plurality of container supports comprises a syringe pump and one machine readable support indicator of the plurality of machine readable support indicators is associated with the syringe pump.

In an 11th aspect according to any one of aspects 1 to 10, wherein the computing apparatus is configured to identify one or more possible selected treatments based at least in part on the association between an identified solution and an identified container support.

In a 12th aspect according to any one of aspects 1 to 10, wherein the system comprises an input device operably coupled to the computing apparatus, and wherein the computing apparatus is configured to receive a signal from the input device identifying the selected treatment.

In a 13th aspect according to any one of aspects 1 to 12, wherein the sensor is movable relative to the renal insufficiency treatment apparatus.

In a fourteenth aspect, a method for verifying solution used in a renal insufficiency treatment as described herein includes: providing a renal insufficiency treatment system comprising a plurality of container supports; identifying a container support of the plurality of container supports; identifying solution in a plurality of solution containers by reading a machine readable solution indicator on a solution container of the plurality of solution containers; associating the identified solution with the identified container support by reading the machine readable solution indicator on the solution container of the identified solution immediately before or immediately after identifying the container support; attaching the solution container of the plurality of solution containers to the identified container support of the plurality of container supports; verifying, based at least in part on the association between an identified solution and an identified container support, that the identified solution in the solution container associated with the identified container support is compatible with a selected treatment; and issuing an alert if the association between identified solutions and identified container support is not compatible with the selected treatment.

In a 15th aspect according to aspect 14, identifying the container support of the plurality of container supports comprises reading a machine readable support indicator associated with the container support.

In a 16th aspect according to aspect 14, identifying the container support of the plurality of container supports comprises moving the container support between a closed configuration and an open configuration, wherein the container support is configured to receive a solution container when in the open configuration.

In a 17th aspect according to any one of aspects 14 to 16, associating an identified solution with an identified container support comprises associating the first support signal received after the solution signal is received for the identified solution.

In an 18th aspect according to any one of aspects 14 to 16, associating an identified solution with an identified container support comprises associating a first identified solution with a first identified container support for a first pair of identified solution and identified container support that are identified based on a first pair of consecutively identified solution containers and container supports.

In a 19th aspect according to aspect 18, associating an identified solution with an identified container support comprises associating a second identified solution with a second identified container support for a second pair of identified solution and identified container support that are identified based on a second pair of identified solution containers and container supports.

In a 20th aspect according to aspect 19, the selected treatment is identified based on the first and second pairs of associated identified solutions and identified container supports.

In a 21st aspect according to any one of aspects 14 to 20, one or more solution containers are weighed on the container support with which they are associated.

In a 22nd aspect according to aspect 21, an identified solution container is associated with an identified container support when the solution container is weighed by the identified container support before identifying a subsequent solution container by reading the machine readable solution indicator on the subsequent solution container.

In a 23rd aspect according to any one of aspects 14 to 20, one container support of the plurality of container supports comprises a syringe pump and identifying the syringe pump as a container support comprises reading one machine readable support indicator of the plurality of machine readable support indicators associated with the syringe pump.

In a 24th aspect according to any one of aspects 14 to 23, one or more possible selected treatments are identified based at least in part on the association between an identified solution and an identified container support.

In a 25th aspect according to any one of aspects 14 to 23, the selected treatment is identified by a user using an input device operably coupled to the renal insufficiency treatment system.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF ILLUSTRATIVE EMBODIMENTS

Figure 1:
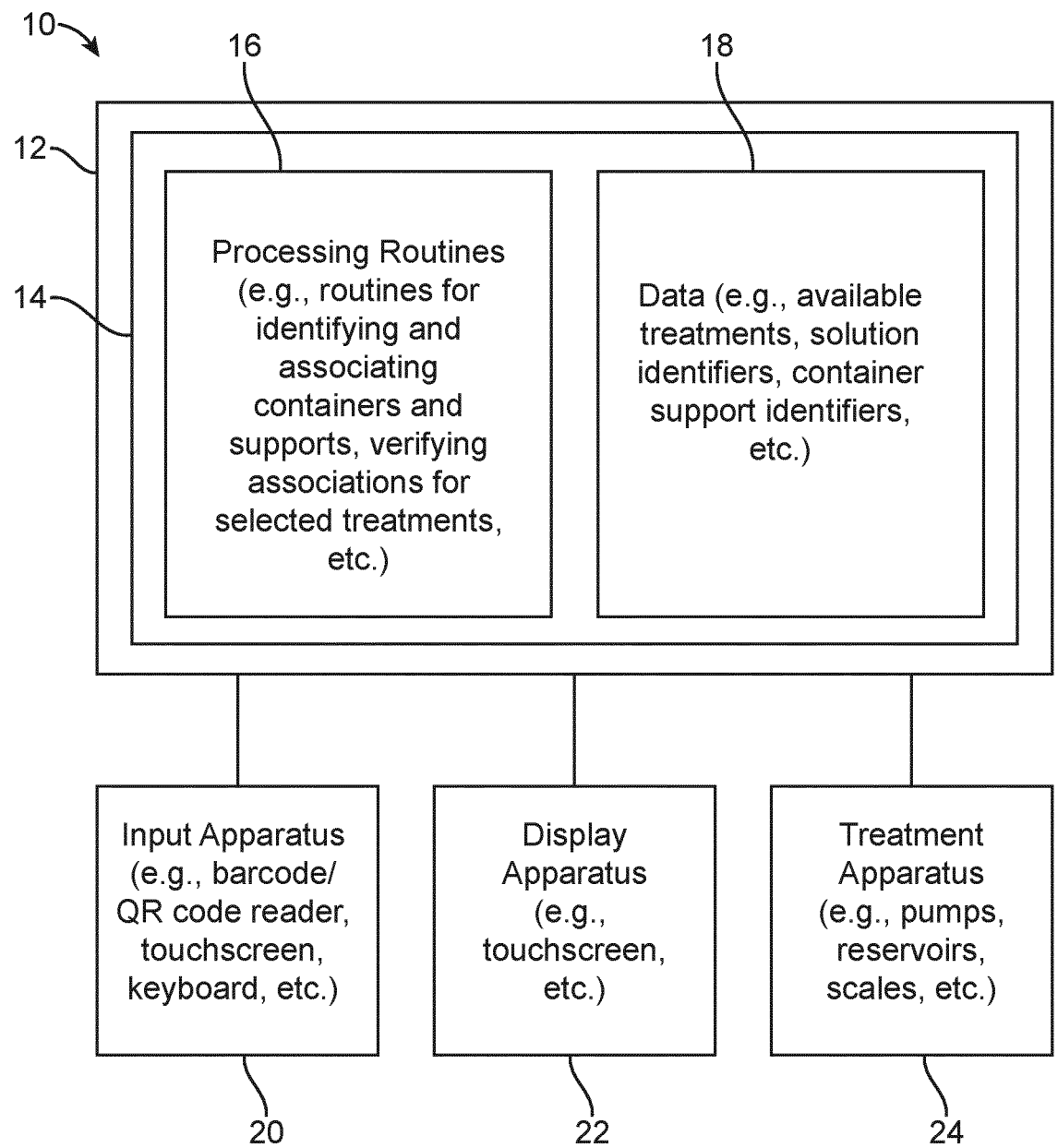
FIG. 1 is a block diagram of an illustrative renal insufficiency treatment system in the form of an extracorporeal blood treatment system including input apparatus, display apparatus, and treatment system that may utilize the methods and processes described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods including identifying and associating a solution with a container support for use in renal insufficiency treatments shall be described with reference to FIGS. 1-5. It will be apparent to one skilled in the art that elements or processes from one embodiment may be used in combination with elements or processes of the other embodiments, and that the possible embodiments of such systems and methods using combinations of features set forth herein is not limited to the specific embodiments shown in the Figures and/or described herein. Further, it will be recognized that the embodiments described herein may include many elements that are not necessarily shown to scale. Still further, it will be recognized that timing and use of the processes described herein may be modified but still fall within the scope of the present disclosure, although certain timings of or use of certain processes may be advantageous over others.

The present disclosure may be described as systems and methods to associate an identified solution with an identified container support and verify compatibility with a selected treatment. For example, an illustrative renal insufficiency treatment system may be configured to scan and/or identify various components of the system (e.g., via indicators such as barcodes, QR codes, identifiers, RFID tags/devices, Near Field Communication (NFC) tags/devices, etc.) to ensure compatibility and compliance for a specific treatment. Specifically, the system may include a sensor (e.g., a scanner, vision system, camera, etc.) that is configured to scan and/or identify indicators associated with solution containers (e.g., bags, reservoirs, syringes, etc.) and container supports (e.g., scales, etc.) used by the system.

These features may assist in tracking and aligning proper concentrations/constituents in solutions that are used during renal insufficiency therapy. For example, an actual concentration being used may be compared with a proposed prescription solution as well as to a selected therapy and expected solutions for that therapy for verification purposes. Further, the renal insufficiency treatment system often already performs multiple calculations to determine fluid flow rates based upon dosage prescriptions and patients body weight, citrate load, post filter hematocrit, etc., therefore, the system may also determine use of the proposed concentrations based upon the prescribed dosages and other treatment parameters.

Further, the sensor may be configured to identify any indicator associated with a solution or support, whether the indicator was previously known or unknown (e.g., using a local or connected database, through information stored within the indicator, etc.). In one or more embodiments, a configuration menu or table may be used to automatically load which solutions citrate concentrations are used and which calcium solutions are used based on the information obtained through the indicator (e.g., using the sensor). Furthermore, in one or more embodiments, a user may input specific conditions associated with a given therapy treatment and the system may verify the applicability of a solution identified by the system. In other words, the system may determine whether selected parameters (e.g., solution type, concentration of calcium or heparin, solution container location, anticoagulation type, etc.) are applicable and appropriate for a specific therapy treatment. In one or more embodiments, this implementation may help prevent errors, may increase safety, and may provide the user with additional data on therapy usages.

An exemplary renal insufficiency treatment system 10 depicted in FIG. 1 may be used to execute, or perform, the exemplary methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery/collection. In at least one embodiment, the system 10 could be a peritoneal dialysis treatment system configured to deliver dialysis fluid to the peritoneal cavity of a patient.

As shown, the exemplary renal insufficiency treatment system 10 includes computing apparatus 12. The computing apparatus 12 may be configured to receive input from input apparatus 20 and transmit output to display apparatus 22.

The treatment apparatus 24 of system 10 may include any apparatus used by an exemplary renal insufficiency treatment system capable of performing renal insufficiency treatments, such as, e.g., pumps, containers/reservoirs, scales, treatment sets, filters, stoppages sensors, pressure sensors, etc. For example, the treatment apparatus 24 may include, in on or more embodiments, one or more elements, or components, of the exemplary extracorporeal blood treatment system described herein with reference to FIG. 2A or 2B.

The exemplary systems, and exemplary methods performed, or used, by such exemplary systems, described herein may be generally referred to as renal insufficiency treatment systems. The general terms "dialysis" and "renal insufficiency treatment" as used herein include peritoneal dialysis as well as hemodialysis, hemofiltration, hemodiafiltration, hemoperfusion, liver dialysis, and therapeutic plasma exchange (TPE), among other similar treatment procedures.

In peritoneal dialysis generally, dialysis fluid is infused into the patient's peritoneal cavity. This cavity is lined by the peritoneal membrane which is highly vascularized. Substances are removed from the patient's blood by diffusion across the peritoneal membrane into the dialysis fluid. Excess fluid (e.g., water) can also be removed by osmosis induced by a hypertonic dialysis fluid (e.g., ultrafiltration).

In extracorporeal blood treatment generally, blood is taken out of the body and exposed to a treatment device to separate substances therefrom and/or to add substances thereto and is then returned to the body. Although extracorporeal blood treatment systems capable of performing general dialysis (as defined above, including TPE) as well as those for infusion of drugs are to be contemplated herein, the illustrative systems may generally be configured to perform continuous renal replacement therapy (CRRT). Additionally, extracorporeal blood treatment systems that perform extracorporeal membrane oxygenation (ECMO), hemoperfusion, liver dialysis, apheresis, TPE, etc. may benefit from the systems, methods, and processes described herein and the present disclosure is not limited to any particular fluid processing system.

Figure 2A:
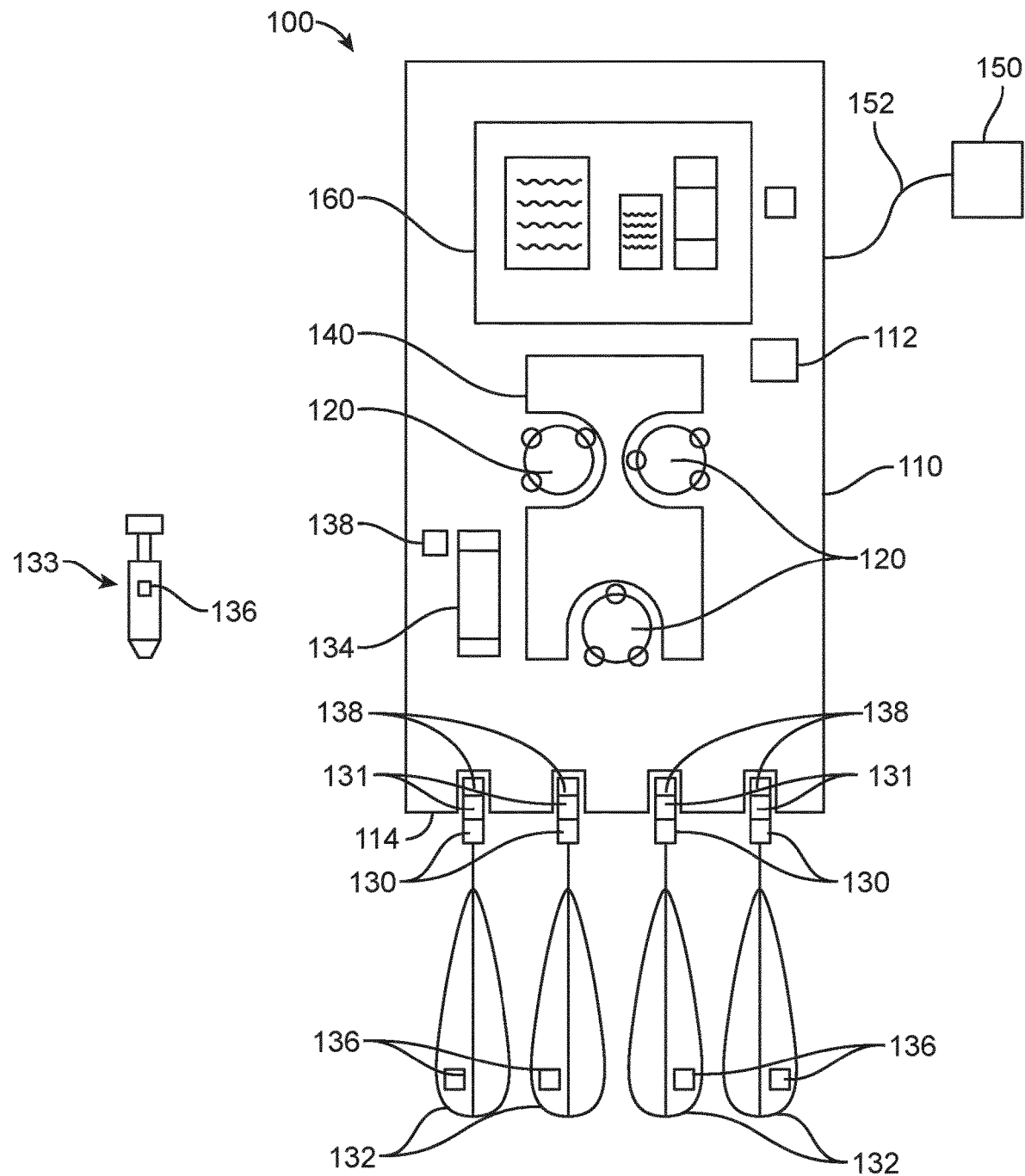
FIG. 2A is an illustrative extracorporeal blood treatment system that may utilize the methods and processes described herein.

Referring to FIG. 2A, one illustrative embodiment of a renal insufficiency treatment system in the form of an extracorporeal blood treatment system 100 is depicted. The system 100 includes a housing 110 having a computing apparatus 112. The system 100 further includes one or more pumps 120, one or more disposable elements 140 (e.g., including or part of integrated modules), and one or more sensors 150 for use in performing one or more extracorporeal blood treatments. The one or more pumps 120 may be used to move liquids through the system as part of a treatment process. Although the pumps 120 are depicted in the form of peristaltic pumps, the pumps used in the extracorporeal blood treatment system described herein may be provided in a variety of alternative forms, e.g., piston pumps, pumps for use with syringes, diaphragm pumps, etc. The one or more pumps 120 may include one or more dialysate pumps and one or more effluent pumps. The dialysate pumps may be generally described as being on the upstream side of a blood treatment unit (e.g., a filter) on a dialysate circuit, and the effluent pumps may be generally described as being on the downstream side of the blood treatment unit on the dialysate circuit.

The one or more disposable elements 140 may be coupled to the system 100 for use in performing the extracorporeal blood treatment. The one or more disposable elements 140 may include one or more fluid circuits such as, e.g., dialysis or dialysate fluid circuits, blood circuits, etc. and/or one or more blood treatment units such as, e.g., filters, etc. In at least one embodiment, a disposable element 140 is a cartridge or integrated unit including a plurality of various parts or portions configured to perform the extracorporeal blood treatment. Additionally, the one or more disposable elements 140 may include containers, or vessels, containing, or holding, one or more substances for use in the performance of the extracorporeal blood treatment. For example, a disposable element 140 may include a container, or vessel, holding bicarbonate, citrate, calcium, dextrose, glucose, and/or dialysate/dialysis fluid, which may be operatively coupled to the dialysis/dialysate fluid circuit. Further, the disposable elements 140 may be described as providing at least a portion of the extracorporeal blood treatment fluid circuit that may be operatively coupled to one or more pumps 120 and one or more sensors of the system 100 for use in performing extracorporeal blood treatments. As shown, a disposable element 140 appears to be coupled to the housing 110 of the system 100 to, e.g., integrate with the one or more other fluid circuits, pumps 120, and sensors of the system 100.

As described herein, the one or more disposable elements 140 may be described as including one or more disposable fluid circuits and one or more blood treatment units operatively coupled to the one or more disposable fluid circuits. The one or more disposable elements 140 may be further described as including a blood circuit for receiving, circulating, and returning blood from/to a patient. The blood circuit may include one or more blood lines (e.g., as part of a disposable element). For example, the system 100 may include a blood pump configured to move blood through an extracorporeal circuit during extracorporeal blood treatment. Further, the one or more disposable elements 140 may be further described as including a dialysis/dialysate circuit operatively coupled, or couplable, to the blood circuit to remove waste from the blood of the patient. The dialysis/dialysate circuit may receive, circulate, and return dialysis/dialysate fluid (e.g., returning dialysis/dialysate fluid including waste). The dialysis/dialysate circuit may include one or more dialysis/dialysate lines (e.g., as part of a disposable element 140). The blood treatment units may be, for example, a plasma filter, a hemodialysis filter, a hemofiltration filter, etc. Generally, the blood treatment units may be referred to as "filters."

Additionally, the extracorporeal blood treatment fluid circuit of the system 100 may be described as being completed by a combination of the disposable elements 140 and the system 100 and may be generally described as defining a blood circuit that removes blood from a patient, for example, via a catheter inserted in a vascular access of the patient, and takes the blood though a blood removal line. Then, the blood may pass through a chamber (e.g., a blood chamber) and, via a return line, may be transported back to the patient.

The treatment system 100 also includes, in one or more embodiments, a display 160 used to convey information to an operator or user. The display 160 may also serve as an input device if, e.g., the display 160 is in the form of a touchscreen. Also, although the display 160 is depicted as being located in the housing 110, in one or more embodiments, the display 160 may be separate from the housing 110 of the extracorporeal blood treatment system 100. For example, the display 160 may be movably (e.g., swivel, tilt, etc.) attached, or coupled, to a top end of the housing 110.

The extracorporeal blood treatment system 100 also includes a plurality of container supports 130. Each of the container supports 130 of the plurality of container supports 130 may be configured to receive and hold (e.g., support) a solution container 132. The container supports 130 may take any suitable shape and form. For example, in one or more embodiments, the container supports 130 may include scales 131, a syringe pump 134, etc. The scales 131 may be configured to weigh the solution container that the scale 131 is supporting (i.e., may be another type of sensor for the system 100). The container support 130 may be positioned below a bottom end 114 of the housing (e.g., as shown in FIG. 2), at least in part because the solution containers 132 may typically attach to and hang from the container supports 130. However, the container supports 130 may be positioned in any suitable location relative to the housing 110. Further, although the depicted embodiment of extracorporeal blood treatment system 100 includes four container supports 130 and associated solution containers 132, other embodiments of an extracorporeal blood treatment system as described herein may include one or more container supports 130 and associated solution containers 132 such as, e.g., as few as two container supports 130 and associated solution containers 132, three container supports 130 and associated solution containers 132, four or more container supports 130 and associated solution containers 132, etc.

In the embodiment shown, the solution containers 132 may be in the form of, e.g., flexible polymeric bags configured to hold liquids or a syringe 133. Solution containers 132, however, used in connection with the exemplary extracorporeal blood treatment systems described herein may take any suitable form in which liquids can be stored and weighed by any scale or weighing apparatus, e.g., bottles, tanks, cartons, jugs, etc.

In one or more embodiments, the system 100 may provide an indication that a solution container 132 attached to a container support 130 including a scale 131 has passed a selected weight limit as a part of monitoring the status of the solution containers 132. That selected weight limit may, in the case of a solution container 132 used to collect liquids from the extracorporeal blood treatment system, be an upper limit such that passing (e.g., reaching and/or exceeding) the selected weight limit is an indication that the solution container 132 is reaching or has reached its loading capacity and may need to be replaced with a solution container 132 having more capacity to collect liquid. In the case of a solution container 132 used to supply liquids to the extracorporeal blood treatment system, the selected weight limit may be a lower limit such that passing (e.g., reaching and/or falling below) the selected weight limit is an indication that the solution container 132 is reaching or has reached a level at which the solution container 132 may need to be replaced with a fresh solution container 132 containing additional liquid to be supplied to the extracorporeal blood treatment system 100.

As shown in FIG. 2A, the system 100 may include an indicator 136, 138 associated with (e.g., positioned proximate) each of the solution containers 132 and each of the container supports 130, respectively. Each of the indicators 136, 138 may represent unique information (e.g., retrieved from a library or database) pertaining to the solution container 132 or container support 130 for which it is associated. For example, the indicator 136 associated with a solution container 132 may identify a citrate solution, a replacement solution, a dialysis solution, infusion fluid, etc. and the indicator 138 associated with a container support 130 may identify a pre-blood pump scale, a dialysate scale, a replacement scale, etc.

Specifically, each solution container 132 (e.g., reservoirs, syringes 133, etc.) may include a machine readable solution indicator 136 configured to identify solution in the solution container 132. For example, the machine readable solution indicator 136 may contain data or information relevant to the solution container 132 for which it is associated. Specifically, the data or information from the machine readable solution indicator 136 may describe the type of solution or the concentration of a specific solution. The machine readable solution indicator 136 may take any suitable form and size. For example, the machine readable solution indicator 136 may include a barcode (e.g., Unique Identification Barcode (UDI), etc.), a QR code, RFID tags/devices, Near Field Communication (NFC) tags/devices, visions systems with object recognition software, etc. The machine readable solution indicator 136 may be located anywhere on the solution container 132 to associate the machine readable solution indicator 136 with the solution container 132. In one or more embodiments, the machine readable solution indicator 136 may be located on packaging used to store and/or transport the solution container 132.

In one or more embodiments, the solution container 132 may include a syringe 133 that has an indicator 136 to identify the type of solution (e.g., calcium or heparin) contained therein. Similar to other solution containers 132 described herein, the indicator 136 associated with the syringe 133 may be used to compare the solution within the syringe 133 (e.g., defining a concentration of calcium or heparin) with the solution expected by the system 100 for a specific therapy. Therefore, the actual syringe solution may be compared with the expected syringe solution and verified by the system 100.

Similarly, each container support 130 (e.g., scales, syringe pumps 134, etc.) may include a machine readable support indicator 138 configured to identify the container support 130. For example, the machine readable support indicator 138 may contain data or information relevant to the container support 130 for which it is associated. Specifically, the data or information from the machine readable support indicator 138 may describe the type of support and, e.g., which type of solution container 132 should be supported thereon. The machine readable support indicator 138 may take any suitable form and size. For example, the machine readable solution indicator 136 may include a barcode (e.g., Unique Identification Barcode (UDI), etc.), a QR code, RFID tags/devices, Near Field Communication (NFC) tags/devices, visions systems with object recognition software, Bluetooth, etc. The machine readable support indicator 138 may be located anywhere on the system 100 to readily associate the machine readable support indicator 138 with the corresponding container support 130. For example, as shown in FIG. 2, the machine readable support indicator 138 may be physically located on the container support 130. As shown in FIG. 3, the machine readable support indicator 138 may be located on the housing 110 at a location proximate the corresponding container support 130. In one or more embodiments, each machine readable support indicator 138 may be located such that it is closer to the corresponding container support 130 than any other container support 130.

Further, the system 100 may include a sensor 150 configured to read one or both of the machine readable solution indicator 136 and the machine readable support indicator 138. Thereafter, the sensor 150 may transmit the data or information (e.g., one or more signals) read from the indicators 136, 138 to the computing apparatus 112 to identify the components associated with the read indicators 136, 138. The sensor 150 may be any suitable device configured to capture and relay the data or information contained within the indicators 136, 138. For example, the sensor 150 may be described as a scanner, a reader, a camera, Near Field Communication (NFC) device, etc.

In one or more embodiments, the computing apparatus 112 may interpret the data or information obtained from the indicators 136, 138 through a database or library. In one or more embodiments, a user may modify the database or library (e.g., using a template in the system configurations) to include additional or new solution compositions (e.g., with various concentrations of constituents in each of the additional or new solutions). Further, in one or more embodiments, each solution may be associated with a specific part number or portion of an indicator (e.g., barcode, QR code, NFC tag, etc.) that helps to verify the information conveyed by the indicator. Verification of the information (i.e., by using error correction, redundancy, etc.) received from the indicator may be important to help prevent the information from being misread and incorrectly identified.

Additionally, in one or more embodiments, information or data tied to the indicator associated with a solution may also include, e.g., lot numbers, date of manufacturing, expiry date, etc. This information may be utilized by the system to identify the source and lifespan of a particular solution to, e.g., prevent use of an expired product. Verification of this additional information may also be important to avoid misreading and/or erroneously discarding a solution based on this information.

The sensor 150 may be described as an input apparatus 20 as it pertains to FIG. 1. Therefore, the sensor 150 may be operably coupled to the computing apparatus 12/112 such that the sensor 150 may transmit signals to the computing apparatus 12/112. Additionally, a connection 152 may be provided between the sensor 150 and the housing 110 to operably couple the sensor 150 to the computing apparatus 12/112. For example, the connection 152 may include an electrical connection or a wireless connection.

Further, in one or more embodiments, the sensor 150 may be movable relative to the housing 110 and, in other embodiments, the sensor 150 may be fixed relative to the housing 110. For example, in such embodiments that the sensor 150 may be movable relative to the housing 110 (and, e.g., only limited in movement by the length of the wired electrical connection or range of the wireless connection), the sensor 150 may move to a location and orientation necessary to scan or read the indicators 136, 138. When the sensor 150 is fixed relative to the housing 110, the indicators 136, 138 may be moved to a location and orientation such that the indicators 136, 138 may be scanned or read by the sensor 150. For example, because the solution containers 132 are replaceable and, therefore, movable, each solution container 132 may be moved to a location to be read or scanned prior to being installed in the system 100. On the other hand, the container supports 130 are often fixed or have limited mobility relative to the housing 110. As such, in one or more embodiments, data or information to identify a container support 130 may be transmitted to the computing apparatus 12 without scanning or reading a machine readable support indicator 138, as will be described later herein.

Figure 2B:
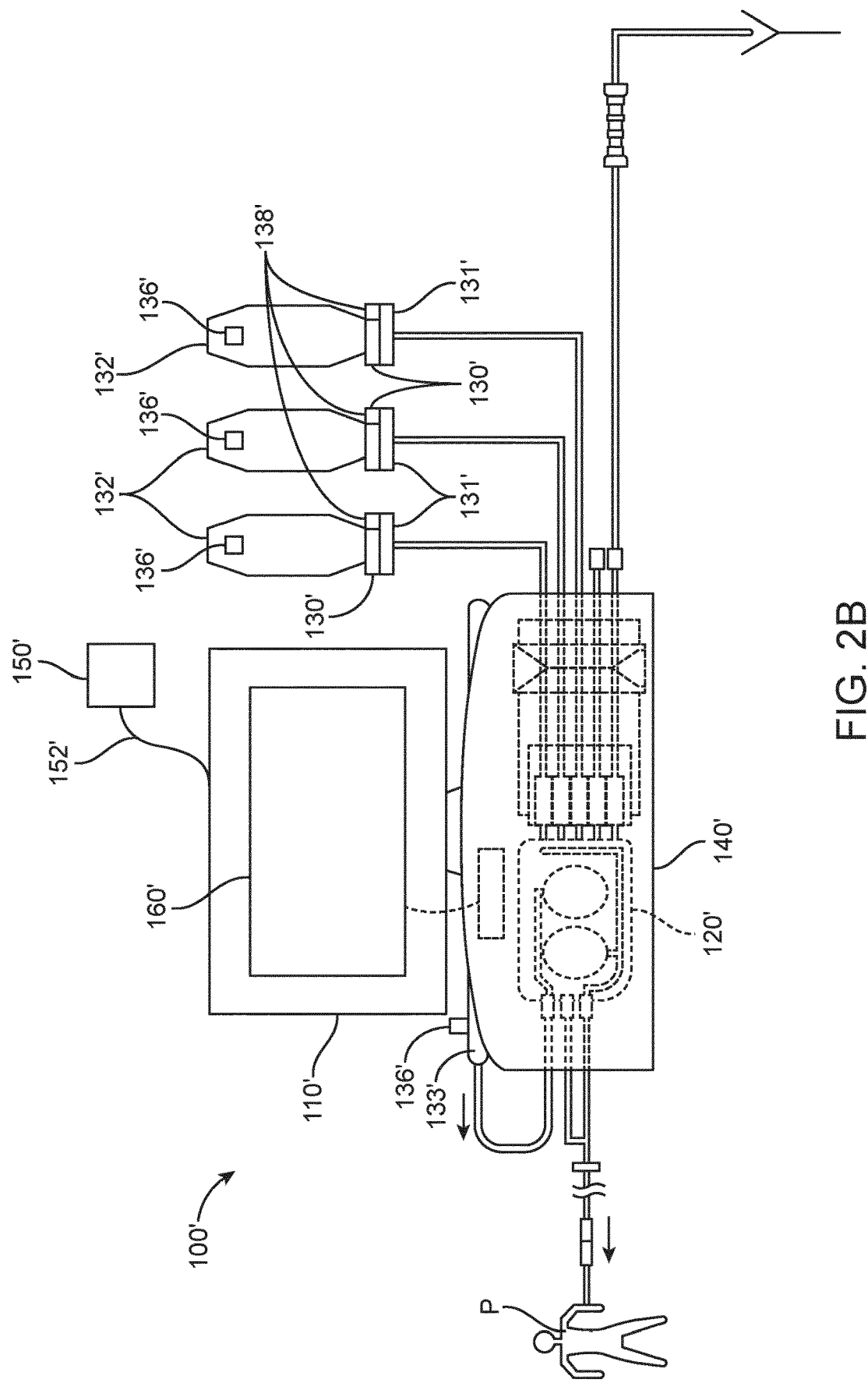
FIG. 2B is an illustrative peritoneal dialysis system that may utilize the methods and processes described herein.
Figure 3:
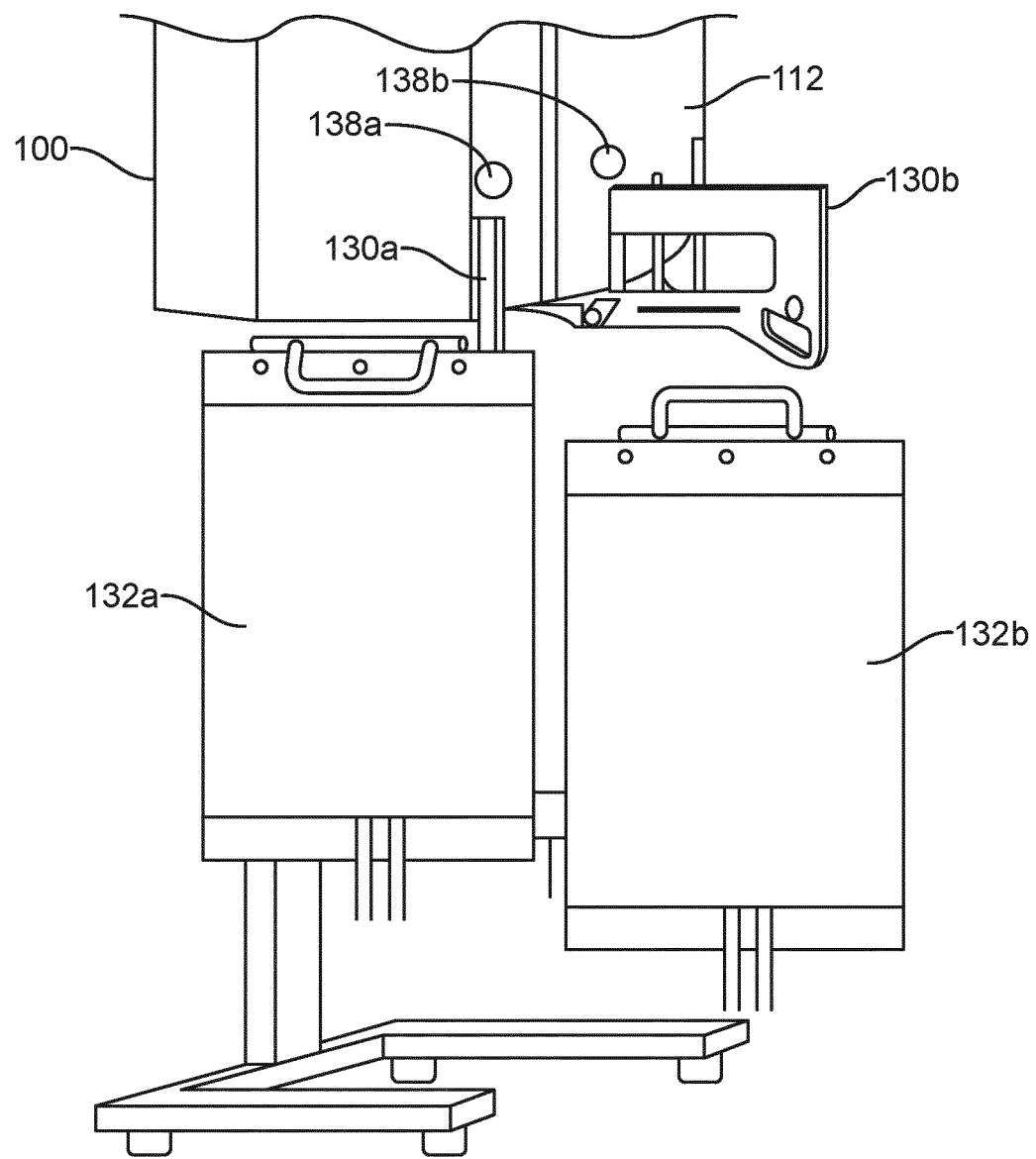
FIG. 3 is an expanded view of a portion of the illustrative extracorporeal blood treatment system of FIG. 2A.

While the illustrative embodiment of a renal insufficiency treatment system in the form of an extracorporeal blood treatment system 100 is depicted and described in connection with FIG. 2A, one illustrative embodiment of a renal insufficiency treatment system in the form of a peritoneal dialysis system 100' is depicted in FIG. 2B. The system 100' includes computing apparatus contained in housing 110', pumps 120', a disposable element 140', sensor 150', and a user interface 160' (which may, as described herein, be both a display and an input device (e.g., a touchscreen, etc.)).

The system 100' may include container supports 130' to support containers 132' containing one or more solutions used to prepare a peritoneal dialysis solution in container 133' that is to be delivered to the peritoneal cavity of a patient P to perform peritoneal dialysis. Each of container supports 130' may include an indicator 138' associated with a selected container support 130'. Each of the containers 132' and 133' may include a machine readable solution indicator 136' configured to, e.g., identify a solution in the container 132'/133'.

The pumps 120' may be used to move liquids through the system as part of a treatment process, including moving solutions from the containers 132' to container 133' and/or from container 133' to the patient P.

System 100' further includes a sensor 150' and connection 152' connecting sensor 150' to a housing 110' of the system 100', the sensor 150' configured to read the machine readable solution indicators 136' on the solution containers 132'/133' as described herein. The sensor 150' may further be configured to read the machine readable indicators 138' on the container supports 130' to identify the container support 130' as described herein.

As shown in FIG. 1 and as related to FIGS. 2A and 2B, the treatment apparatus 24 may be operatively coupled, or connected, to the computing apparatus 12. The treatment apparatus 24 operably coupled to the computing apparatus 12 may include the pumps 120/120' and container supports 130/130' as shown in FIGS. 2A and 2B. Further, the input apparatus 20 operably coupled to the computing apparatus 12 may include the sensor 150/150'. For example, the computing apparatus 12 may be configured to receive one or more signals (e.g., data or information, solution signal, support signal, etc.) from the sensor 150/150' to identify the solution container 132/132' and/or the container support 130/130'.

Figure 4:
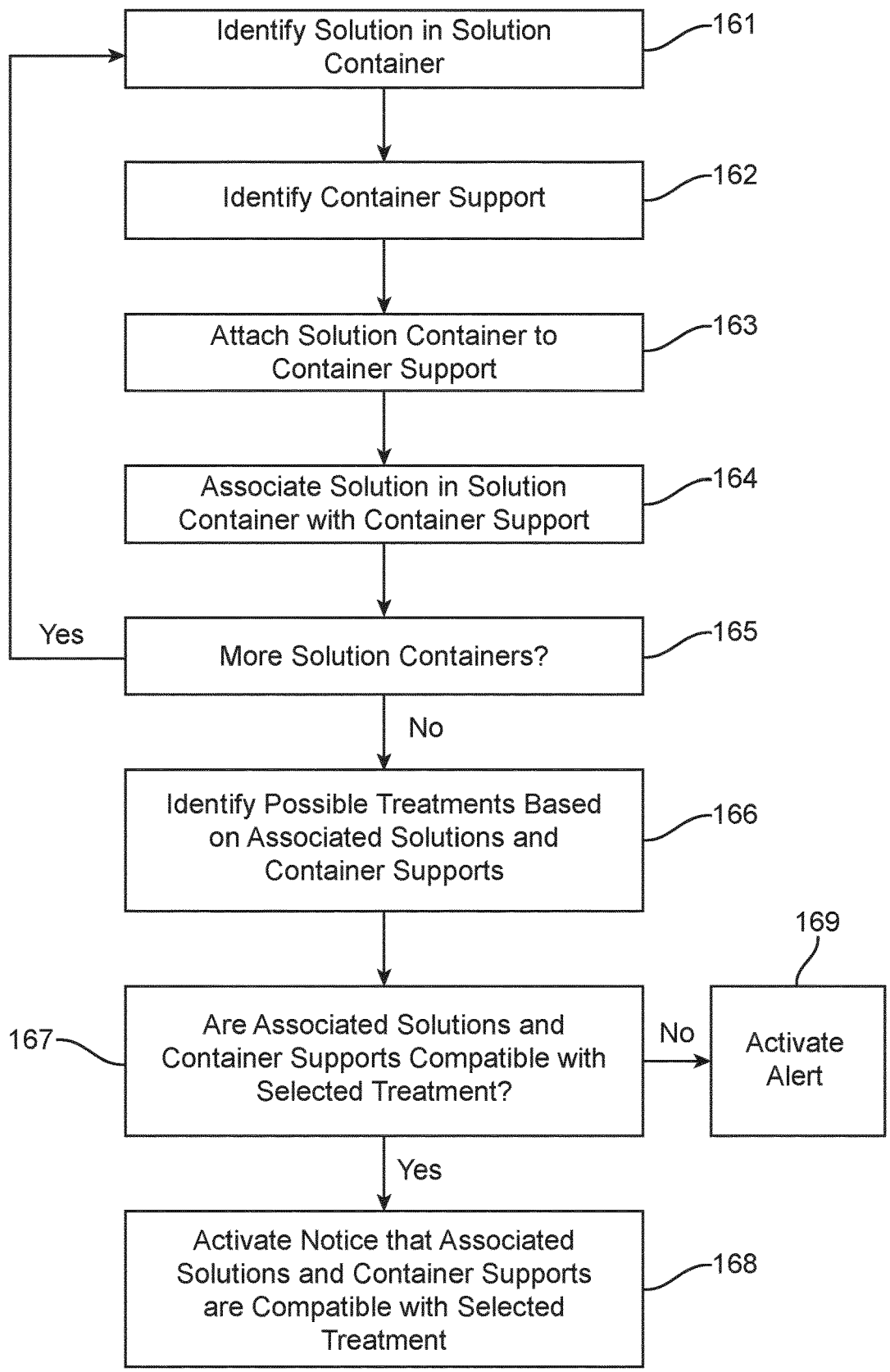
FIG. 4 is a flow diagram of an illustrative method of identifying possible treatments based on identified and associated solutions and container supports for use in renal insufficiency treatment systems, e.g., such as shown generally in FIGS. 1-3.
Figure 5:
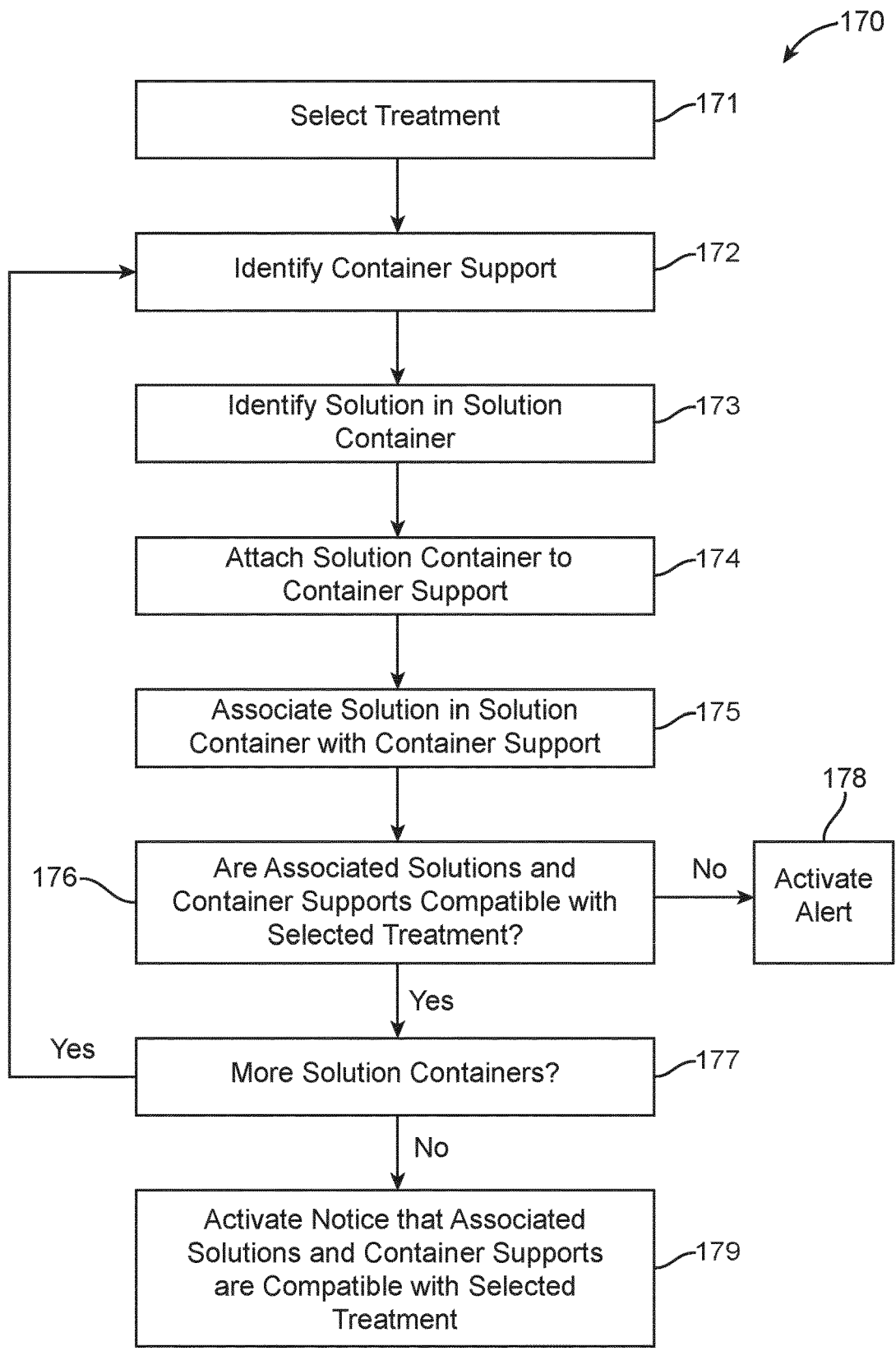
FIG. 5 is a flow diagram of an illustrative method of selecting a treatment and determining if identified and associated solutions and container supports are compatible therewith for use in renal insufficiency treatment systems, e.g., such as shown generally in FIGS. 1-3.

The computing apparatus 12 may be configured to verify solutions prior to therapy in various different ways, for example, as shown in the illustrative methods depicted in FIGS. 4 and 5. For example, as shown in method of FIG. 4, the computing apparatus 12 may be configured to identify the solution containers 132/132' and the associated container supports 130/130', and then identify the possible therapy treatments based on those identified solutions and supports. In other words, at the time of setup, the user may be requested to scan (e.g., using the sensor 150/150') the indicator 136/136' associated with a solution container 132/132' followed by scanning the indicator 138/138' associated with a container support 130/130' (or vice versa) upon which the solution container 132/132' will be supported. The system 100 may be configured to provide the user with applicable therapies (e.g., through a display) for that specific solution container 132/132' positioned on that specific container support 130/130'.

For example, if the system is an extracorporeal blood treatment system with solution containers 132 including dialysate solution were supported on the replacement and dialysate scales or supports 130, the system 100 may suggest or display a continuous veno-venous hemodialysis (CVVHD) therapy, and if a solution container 132 including citrate solution was supported on the pre-blood pump scale, the system 100 may suggest or display citrate-calcium anticoagulation or citrate only anticoagulation.

Specifically, the computing apparatus 12 may be configured to identify 161 solution in the solution container 132/132'. In one or more embodiments, the computing apparatus 12 may be configured to identify the solution in the solution container 132/132' based on a solution signal received from the sensor 150/150' in response to reading the machine readable solution indicator 136/136' associated with the solution container 132/132'. In other words, the sensor 150/150' may read or scan the machine readable solution indicator 136/136' located on or associated with the solution container 132/132' and generate a solution signal that may be sent to the computing apparatus 12.

Also, the computing apparatus 12 may be configured to identify 162 the container support 130/130'. For example, the computing apparatus 12 may be configured to identify 162 the container support 130/130' based on a support signal received by the computing apparatus 12. The support signal may be generated in any suitable way. In one or more embodiments, the support signal may be generated by the sensor 150/150' reading or scanning the machine readable support indicator 138/138' associated with the container support 130/130'. In other words, the container support 130/130' may be identified (e.g., by the computing apparatus 12) based on the support signal received from the sensor 150/150' in response to reading the machine readable support indicator 138/138'.

In other embodiments, the container support 130/130' may be operably coupled to the computing apparatus 12 and configured to provide the support signal to the computing apparatus 12 (e.g., without the use of the sensor 150/150'). In other words, the system 100/100' may be configured to identify the container support 130/130' during the process of loading the container support 130/130' with a solution container 132/132' (e.g., when replacing the solution container 132/132'). For example, the container support 130/130' may be movable between an open configuration and a closed configuration, and the support signals may be generated based on moving the container support 130/130' between configurations. As shown in FIG. 3, container support 130b is in the open configuration and configured to receive a solution container 132b and container support 130a is in the closed configuration with a solution container 132a supported thereon.

In one or more embodiments, the support signals for each container support 130/130' of the plurality of container supports 130/130' may be generated by moving each container support 130/130' between the open configuration and the closed configuration. For example, the support signal may be generated when the container support 130/130' moves from the closed configuration to the open configuration, the support signal may be generated when the container support 130/130' moves from the open configuration to the closed configuration, or the support signal may be generated when the container support 130/130' moves from the closed configuration to the open configuration and back to the closed configuration. Specifically, when the container support 130/130' is placed in a position to receive a solution container 132/132' (e.g., when moved to or positioned in an open or unlocked position, etc.), the system 100/100' may identify that specific container support 130/130'. In other words, due to an act of opening the container support 130/130' to receive a solution container 132/132', the system 100/100' may associate that container support 130/130' with the solution container 132/132' identified immediately before or after the act of opening the container support 130/130'. As such, this feature may eliminate the need to receive data or information from (e.g., via scanning or reading) an indicator 138/138' associated with the container support 130/130' (e.g., because the act of opening or unlocking automatically transmits that data or information). It is noted that, in one or more embodiments, the generation of the support signal may be connected to the container support 130/130' sensing a solution container 132/132' loaded thereon (e.g., using a weight sensor).

Further, the method illustrated in FIG. 4 may include attaching 163 the solution container 132/132' to the container support 130/130'. In other words, after each of the solution container 132/132' and the container support 130/130' are identified, the identified solution container 132/132' may be attached to the identified container support 130/130' in an operating position. Thereafter, the computing apparatus 12 may be configured to associate 164 the solution in the identified solution container 132/132' with the identified container support 130/130'. In one or more embodiments, the computing apparatus 12 may be configured to associate the identified solution with the identified container support 130/130' for the first support signal received after the solution signal is received (e.g., by the computing apparatus 12) for the identified solution. In other words, after the solution container 132/132' is identified by the computing apparatus 12, the next support signal received by the computing apparatus 12 associates the identified solution container 132/132' with the identified container support 130/130' (e.g., based on the support signal). In other embodiments, the container support 130/130' may be identified first and the solution signal generated thereafter may associate the identified solution container 132/132' (e.g., from the solution signal) with the identified container support 130/130'.

As described herein, the container supports 130/130' may include a scale 131/131' configured to weigh a solution container 132/132' supported on the container support 130/130'. In one or more embodiments, each container support 130/130' may be operably coupled to the computing apparatus 12 such that the computing apparatus 12 is configured to receive a weight signal from each container support 130/130' that is indicative of a weight of a solution container 132/132' on the container support 130/130'. Further, the computing apparatus 12 may be configured to associate an identified solution container 132/132' with an identified container support 130/130' only if, after identifying a solution and identifying a container support 130/130', the weight signal is received from the identified container support 130/130' before a subsequent solution signal or a subsequent support signal is received by the computing apparatus 12. In other words, the computing apparatus 12 may confirm that the container support 130/130' actually received the solution container 132/132' that was identified (e.g., due to the change in weight).

After associating 164 the solution of the identified solution container 132/132' with the identified container support 130/130', the method may include querying 165 whether any additional solution containers 132/132' will be added. If more solution containers 132/132' are yet to be added to the system 100/100', the method returns to the step of identifying 161 the solution in the next solution container 132/132'. If there are no additional solution containers 132/132' to add to the system 100/100', the method proceeds to identifying 166 possible therapy treatments. In one or more embodiments, the step of querying 165 whether additional solution containers 132/132' will be added may be shown to the user on the display 160/160'. In one or more embodiments, the user may respond to the query using an input apparatus 20 such as, e.g., keyboard, touchscreen, sensor, etc. For example, in one or more embodiments, the user may scan or read (e.g., using the sensor 150/150') an indicator 136 associated with the next solution container 132/132' to affirmatively respond that an additional solution will be added, thereby restarting the process of identifying solution containers 132/132' and container supports 130/130'.

Therefore, in one or more embodiments, the system 100/100' may identify and associate one or more pairs of solution containers 132/132' and container supports 130/130'. For example, receiving one or more signals from the sensor 150/150' may include receiving a first pair of consecutive support and solution signals (e.g., from the sensor 150/150'). While the pair of signals may be described as consecutive, the signals may be received in any suitable order (e.g., support signal first and solution signal second or solution signal first and support signal second). Further, identifying a container support 130/130' and identifying a solution container 132/132' may include identifying a first pair of container support 130/130' and solution container 132/132' based on the first pair of consecutive support and solution signals. Further yet, associating the identified solution container 132/132' with the identified container support 130/130' may include associating the first identified solution container 132/132' with the first identified container support 130/130'.

Similarly, the system 100/100' may identify and associate a second pair of solution containers 132/132' and container supports 130/130'. For example, receiving one or more signals from the sensor may include receiving a second pair of consecutive support and solution signals (e.g., from the sensor 150/150'). Further, identifying a container support 130/130' and identifying a solution container 132/132' may include identifying a second pair of container support 130/130' and solution container 132/132' based on the second pair of consecutive support and solution signals. Further yet, associating the identified solution container 132/132' with the identified container support 130/130' may include associating the second identified solution container 132/132' with the second identified container support 130/130'.

Once all of the solution containers 132/132' and the container supports 130/130' are identified 161, 162 and associated 164, the computing apparatus 12 may be configured to identify 166 one or more possible treatments based at least in part on the association between the identified solution (e.g., from the identified solution container 132/132') and the identified container support 130/130'. Further, in one or more embodiments, the computing apparatus 12 may be configured to identify the possible treatments based on any number of pairs (e.g., the first and second pairs as described herein) of associated identified solution containers 132/132' and identified container supports 130/130'. In one or more embodiments, the one or more possible treatments may be shown and/or selectable from the display 160/160'. The computing apparatus 12 may be configured to allow the user to make a selection of the desired therapy treatment. For example, the user may use an input device (e.g., using a touchscreen or any other suitable input apparatus 20) of the input apparatus 20 that is operably coupled to the computing apparatus 12 to make the selection because, for example, the computing apparatus 12 may be configured to receive a signal from the input device identifying the selected treatment.

After desired therapy treatment is selected, the computing apparatus 12 may be configured to verify 167 whether the identified solution container 132/132' and the identified container support 130/130' are compatible with the selected treatment to be performed by the system 100/100'. In one or more embodiments, this verification process may be based at least in part on the association between the identified solution container 132/132' and the identified container support 130/130'. If the computing apparatus 12 determines that the identified solution container 132/132' associated with the identified container support 130/130' is not compatible with the selected treatment, the computing apparatus 12 may activate 169 an alert apparatus. The alert apparatus may be any suitable alert (e.g., visual, audial, tactile, etc.) that notifies the user of the potential lack of compatibility. The alert apparatus may be located at any position on the system that may assist the user in noticing the alert. For example, the alert apparatus may be shown on the display 160/160', on the housing 110, proximate the container supports 130/130', etc. If the computing apparatus 12 determines that the identified solution container 132/132' associated with the identified container support 130/130' is compatible with the selected treatment, the computing apparatus 12 may activate 168 a notice that the associated solutions and container supports 130/130' are compatible with the selected treatment. The notice of compatibility may use the same alert apparatus, however with a different notifier, or may inform the user using something different than the alert apparatus.

As described above, another type of verification process is shown as method 170 in FIG. 5. For example, the computing apparatus 12 may receive input from the user selecting a specific therapy treatment before identifying the solution containers 132/132' and the associated container supports 130/130', and then the computing apparatus 12 may be configured to determine whether the selected therapy treatment is compatible with the identified solutions and supports. In other words, the user may enter one or more of a prescription, a method of anti-coagulation, prescribed flow rates and expected solutions (e.g., parameters of a specific therapy), and the system 100/100' may identify whether a specific solution container 132/132' and a specific container support 130/130' (e.g., identified through the indicator 136/136', 138/138') are in conflict with the users selections.

For example, method 170 may include steps that are similar or identical to steps described for method illustrated in FIG. 4. However, method 170 includes selecting 171 a treatment therapy prior to identifying and associating container supports 130/130' and solution containers 132/132'. For example, the user may select a desired treatment using an input device (e.g., using a touchscreen or any other suitable input apparatus 20) of the input apparatus 20 that is operably coupled to the computing apparatus 12. Thereafter, the computing apparatus 12 may be configured to identify 172 the container support 130/130' (e.g., through a machine readable support indicator 138/138', through movement of the container support 130/130', etc.) and identify 173 solution in the solution container 132/132' (e.g., through a machine readable solution indicator 136/136'). The solution container 132/132' may then be attached 174 to the container support 130/130' and the computing apparatus 12 may associate 175 the solution in the identified solution container 132/132' with the identified container support 130/130'.

Further, the computing apparatus 12 may verify 176 whether the associated solution container 132/132' and container support 130/130' are compatible with the pre-selected therapy treatment. If the associated solution container 132/132' and container support 130/130' are not compatible with the selected treatment, an alert apparatus is activated 178. In other words, the system 100/100' may be configured to display a graphic (e.g., on the graphical user interface) that provides feedback (e.g., through a marking representing a correct matching or incorrect matching) to the user during the process regarding whether the components being used are compatible for a specific therapy. Further, if a conflict arises, the system 100/100' may request that either one of the parameters of the specific therapy are changed or the specific solution container 132/132'/container support 130/130' is changed (e.g., to align the solution container 132/132' with the prescribed solution). In one or more embodiments, the system 100/100' may be configured to suggest alterations to correct any conflict. If the associated solution container 132/132' and container support 130/130' are compatible with the selected treatment, a notice is activated 179 indicating that the associated solution and container support 130/130' are compatible with the selected treatment. In one or more embodiments in which the remainder of the system is ready, a treatment could be initiated and/or resumed upon confirmation that the associated solution and container support 130/130' are compatible with the selected treatment.

With reference to FIG. 1, the computing apparatus 12 used in the renal insufficiency systems described herein may include data storage 14 to, e.g., allow for access to processing programs or routines 16 and one or more other types of data 18 that may be employed to carry out exemplary methods and/or processes (e.g., running pumps, identifying solutions and/or containers, associating solutions with containers, verifying compatibility with selected treatment, running a treatment, determining problems with a treatment, exchanging/changing containers/reservoirs, notifying operators/users of problems, displaying status information, etc.) for use in performing renal insufficiency treatments. For example, the computing apparatus 12 may be configured to identify solution containers and container supports, associating the identified solutions and supports, and verifying the compatibility of each with a selected treatment (e.g., described above with respect to FIGS. 2-5).

The computing apparatus 12 may be operatively coupled to the input apparatus 20 and the display apparatus 22 to, e.g., transmit data to and from each of the input apparatus 20 and the display apparatus 22. For example, the computing apparatus 12 may be electrically coupled to each of the input apparatus 20 and the display apparatus 22 using, e.g., analog electrical connections, digital electrical connections, wireless connections, bus-based connections, etc. As described further herein, an operator may provide input to the input apparatus 20 to manipulate, or modify, one or more graphical depictions displayed on the display apparatus 22 to select and view various information such as, for example, identified solutions, identified supports, and treatment options/selections as described herein.

Further, various devices and apparatus may be operatively coupled to the computing apparatus 12 to be used with the computing apparatus 12 to perform one or more renal insufficiency procedures/treatments as well as the functionality, methods, and/or logic described herein. As shown, the system 10 may include input apparatus 20, display apparatus 22, and treatment apparatus 24 operatively coupled to the computing apparatus 12 (e.g., such that the computing apparatus 12 may be configured to use information, or data, from the apparatus 20, 22, 24 and provide information, or data, to the apparatus 20, 22, 24). The input apparatus 20 may include any apparatus capable of providing input to the computing apparatus 12 to perform the functionality, methods, and/or logic described herein.

For example, the input apparatus 20 may include a touchscreen (e.g., capacitive touchscreen, a resistive touchscreen, a multi-touch touchscreen, etc.), a mouse, a keyboard, a trackball, etc. For example, the input apparatus 20 may allow an operator to interact with a graphical user interface including a configuration region for selecting a treatment therapy, which is either based on or verified as compatible with identified solutions and supports as described herein when used in conjunction with the display apparatus 22 (e.g., displaying the graphical user interface).

The display apparatus 22 may include any apparatus capable of displaying information to an operator, such as a graphical user interface, etc., to perform the functionality, methods, and/or logic described herein. For example, the display apparatus 22 may include a liquid crystal display, an organic light-emitting diode screen, a touchscreen, etc. As described further herein, the display apparatus 22 may be configured to display a graphical user interface that includes one or more regions such as a configuration for configuring treatment therapies compatible with identified solutions and supports as well as various other regions and areas.

The processing programs or routines 16 may include programs or routines for performing computational mathematics, matrix mathematics, standardization algorithms, comparison algorithms, or any other processing required to implement one or more exemplary methods and/or processes described herein. Data 18 may include, for example, solution types/concentrations, support types, treatment therapies, patient weight data, container/reservoir mass data, pump data, pump stoppage data, alarm data, fluid data, other flow rates, fluid volumes, heuristics indicative of malfunction, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The program used to implement the methods and/or processes described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and, when executed by a processor, is operable to perform operations such as the methods, processes, and/or functionality described herein.

The computing apparatus 12 may be, for example, any fixed or mobile computer system (e.g., a controller, a microcontroller, a personal computer, minicomputer, etc.). The exact configuration of the computing apparatus 12 is not limiting, and essentially any device capable of providing suitable computing capabilities and control capabilities (e.g., receiving information from indicator, associating identified components, control of renal insufficiency treatment system (e.g., one or more pumps, etc.), etc.) may be used.

As described herein, a digital file may be any medium (e.g., volatile or non-volatile memory, a CD-ROM, etc.) containing digital bits (e.g., encoded in binary, trinary, etc.) that may be readable and/or writeable by computing apparatus 12 described herein. Also, as described herein, a file in user-readable format may be any representation of data (e.g., ASCII text, binary numbers, hexadecimal numbers, decimal numbers, graphically, etc.) presentable on any medium readable and/or understandable by an operator.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed is:

1. A renal insufficiency treatment system comprising:
   a renal insufficiency treatment apparatus comprising a plurality of container supports;
   a plurality of solution containers configured to be supported by the plurality of container supports, wherein each solution container comprises a machine readable solution indicator configured to identify solution in the solution container;
   a plurality of machine readable support indicators, wherein each machine readable support indicator of the plurality of machine readable support indicators is associated with and configured to identify one container support of the plurality of container supports;
   a sensor configured to read the machine readable solution indicators on solution containers and the machine readable support indicators;
   a computing apparatus comprising one or more processors, the computing apparatus operably coupled to the renal insufficiency treatment apparatus and the sensor, wherein the computing apparatus is configured to:
   receive one or more signals from the sensor;
   identify a container support of the plurality of container supports based on a support signal received by the computing apparatus from the sensor in response to reading the machine readable support indicator associated with the container support;
   identify solution in a solution container of the plurality of solution containers based on a solution signal received from the sensor in response to reading the machine readable solution indicator associated with the solution container, the solution signal being received by the computing apparatus;
   associate the identified solution with the identified container support;
   verify, based at least in part on the association between the identified solution and the identified container support, that the identified solution in the solution container associated with the identified container support is compatible with a selected treatment to be performed by the renal insufficiency treatment system; and
   activate an alert apparatus if the identified solution in the solution container associated with the identified container support is not compatible with the selected treatment.

2. The system of claim 1, wherein the container support is operably coupled to the computing apparatus and configured to provide the support signal to the computing apparatus, wherein the support signals for each container support of the plurality of container supports are generated by moving each container support between an open configuration and a closed configuration, wherein each container support is configured to receive a solution container when in the open configuration.

3. The system of claim 1, wherein the computing apparatus is configured to associate an identified solution with an identified container support for the first support signal received after the solution signal is received for the identified solution.

4. The system of claim 1, wherein receiving one or more signals from the sensor comprises receiving a first pair of consecutive support and solution signals from the sensor, wherein identifying a container support and identifying solution comprise identifying a first pair of container support and solution, and wherein associating the identified solution with the identified container support comprises associating the first identified solution with the first identified container support.

5. The system of claim 4, wherein receiving one or more signals from the sensor further comprises receiving a second pair of consecutive support and solution signals from the sensor, wherein identifying a container support and identifying solution comprise identifying a second pair of container support and solution, and wherein associating the identified solution with the identified container support comprises associating the second identified solution with the second identified container support.

6. The system of claim 5, wherein the computing apparatus is further configured to identify the selected treatment based on the first and second pairs of associated identified solutions and identified container supports.

7. The system of claim 1, wherein each container support of the plurality of container supports comprises a scale configured to weigh a solution container supported on the container support, wherein each container support is operably coupled to the computing apparatus, and wherein the computing apparatus is configured to receive a weight signal from each container support that is indicative of a weight of a solution container on the container support.

8. The system of claim 7, wherein the computing apparatus is configured to associate an identified solution with an identified container support only if, after identifying a solution and identifying a container support, a weight signal is received from the identified container support before a subsequent solution signal or a subsequent support signal is received by the computing apparatus.

9. The system of claim 1, wherein one container support of the plurality of container supports comprises a syringe pump and one machine readable support indicator of the plurality of machine readable support indicators is associated with the syringe pump.

10. The system of claim 1, wherein the computing apparatus is configured to identify one or more possible selected treatments based at least in part on the association between an identified solution and an identified container support.

11. The system of claim 1, wherein the system comprises an input device operably coupled to the computing apparatus, and wherein the computing apparatus is configured to receive a signal from the input device identifying the selected treatment.

12. The system of claim 1, wherein the sensor is movable relative to the renal insufficiency treatment apparatus.

13. A method for verifying solution used in a renal insufficiency treatment, the method comprising:
providing a renal insufficiency treatment system comprising a plurality of container supports;
identifying a container support of the plurality of container supports, wherein identifying the container support comprises reading a machine readable support indicator associated with the container support;
identifying solution in a plurality of solution containers by reading a machine readable solution indicator on a solution container of the plurality of solution containers;
associating the identified solution with the identified container support by reading the machine readable solution indicator on the solution container of the identified solution immediately before or immediately after identifying the container support; attaching the solution container of the plurality of solution containers to the identified container support of the plurality of container supports;
verifying, based at least in part on the association between an identified solution and an identified container support, that the identified solution in the solution container associated with the identified container support is compatible with a selected treatment; and
issuing an alert if the association between identified solutions and identified container support is not compatible with the selected treatment.

14. A method according to claim 13, wherein identifying the container support of the plurality of container supports comprises moving the container support between a closed configuration and an open configuration, wherein the container support is configured to receive a solution container when in the open configuration.

15. A method according to claim 13, wherein associating an identified solution with an identified container support comprises associating the first support signal received after the solution signal is received for the identified solution.

16. A method according to claim 13, wherein associating an identified solution with an identified container support comprises associating a first identified solution with a first identified container support for a first pair of identified solution and identified container support that are identified based on a first pair of consecutively identified solution containers and container supports.

17. A method according to claim 16, wherein associating an identified solution with an identified container support comprises associating a second identified solution with a second identified container support for a second pair of identified solution and identified container support that are identified based on a second pair of identified solution containers and container supports.

18. A method according to claim 17, wherein the selected treatment is identified based on the first and second pairs of associated identified solutions and identified container supports.

19. A method according to claim 13, wherein one or more solution containers are weighed on the container support with which they are associated.

20. A method according to claim 19, wherein an identified solution container is associated with an identified container support when the solution container is weighed by the identified container support before identifying a subsequent solution container by reading the machine readable solution indicator on the subsequent solution container.

21. A method according to claim 13, wherein one container support of the plurality of container supports comprises a syringe pump and identifying the syringe pump as a container support comprises reading one machine readable support indicator of the plurality of machine readable support indicators associated with the syringe pump.

22. A method according to claim 13, wherein one or more possible selected treatments are identified based at least in part on the association between an identified solution and an identified container support.

23. A method according to claim 13, wherein the selected treatment is identified by a user using an input device operably coupled to the renal insufficiency treatment system.

* * * * *